United States Patent [19]

Berg et al.

[11] Patent Number: 5,092,966

[45] Date of Patent: Mar. 3, 1992

[54] SEPARATION OF METHYLENE CHLORIDE FROM ETHYL ETHER BY EXTRACTIVE DISTILLATION

[75] Inventors: Lloyd Berg, 1314 S. Third Ave., Bozeman, Mont. 59715; Zuyin Yang, Bozeman, Mont.

[73] Assignee: Lloyd Berg, Bozeman, Mont.

[21] Appl. No.: 678,231

[22] Filed: Apr. 1, 1991

[51] Int. Cl.$^5$ .............. B01D 3/40; C07C 17/38; C07C 41/42
[52] U.S. Cl. .............. 203/57; 203/58; 203/60; 203/62; 203/63; 203/64; 568/699; 570/262
[58] Field of Search .............. 203/60, 64, 62, 58, 203/63, 57; 568/699; 570/262

[56] References Cited

U.S. PATENT DOCUMENTS

| | | | |
|---|---|---|---|
| 3,847,756 | 11/1974 | Statman et al. | 568/699 |
| 4,036,703 | 7/1977 | Leroi et al. | 203/60 |
| 4,121,978 | 10/1978 | Becuwe | 203/60 |
| 4,459,179 | 7/1984 | Berg et al. | 568/699 |

FOREIGN PATENT DOCUMENTS

| | | | |
|---|---|---|---|
| 643135 | 6/1962 | Canada | 568/699 |
| 249870 | 12/1987 | European Pat. Off. | 568/699 |
| 142183 | 6/1980 | German Democratic Rep. | 203/64 |

Primary Examiner—Wilbur Bascomb, Jr.

[57] ABSTRACT

Ethyl ester cannot be completely separated from methylene chloride by conventional distillation or rectification because of the maximum boiling azeotrope. Ethyl ether can be readily separated from methylene chloride by extractive distillation. Typical effective agents are t-butyl alcohol, n-propyl acetate or propoxypropanol.

1 Claim, No Drawings

SEPARATION OF METHYLENE CHLORIDE FROM ETHYL ETHER BY EXTRACTIVE DISTILLATION

FIELD OF THE INVENTION

This invention relates to a method for separating methylene chloride from ethyl ether using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Methylene chloride, B.P. +40° C. forms a maximum boiling azeotrope with ethyl ether, B.P.=34.6° C. at 40.8° C. containing 70% methylene chloride. Extractive distillation would be an attractive method of effecting the separation of methylene chloride from ethyl ether and thus break the azeotrope if agents can be found that (1) will enhance the relative volatility between methylene chloride and ethyl ether and (2) are easy to recover, that is, form no azeotrope with methylene chloride or ethyl ether and boil sufficiently above these two to make the separation by rectification possible with only a few theoretical plates.

Extractive distillation typically requires the addition of an equal amount to twice as much extractive agent as the methylene chloride-ethyl ether on each plate of the rectification column. The extractive agent should be heated to about the same temperature as the plate into which it is introduced. Thus extractive distillation imposes an additional heat requirement on the column as well as somewhat larger plates. However this is less than the increase occassioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the methylene chloride and alcohols otherwise it will form a two phase azeotrope with it and some other method of separation will have to be employed.

TABLE 1

Effect of Relative Volatility on the Separation of Methylene Chloride from Ethyl Ether at 99% Purity

| Relative Volatility | Theoretical Plates | Actual Plates, 75% Efficiency | Actual Plates, 75% Eff., Min. Reflux |
|---|---|---|---|
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employing an effective extractive distillation agent for this separation is shown in Table 1. When ordinary rectification is employed, the maximum azeotrope will be obtained and no separation above 70% methylene chloride will occur. If extractive distillation is used with an agent that converts the relative volatility to 1.7, only 29 actual plates are required to produce methylene chloride and ethyl ether in 99% purity.

OBJECTIVE OF THE INVENTION

The objects of this invention are to provide a process or method of extractive distillation that will enhance the relative volatility of methylene chloride to ethyl ether in their separation in a rectification column. It is a further object of this invention to identify organic compounds that are stable, can be separated from methylene chloride or ethyl ether by rectification with relatively few plates and can be recycled to the extractive distillation column with little decomposition.

SUMMARY OF THE INVENTION

The objects of this invention are provided by a process for the separation of methylene chloride from ethyl ether which entails the use of certain organic compounds as the agent in extractive distillation.

DETAILED DESCRIPTION OF THE INVENTION

We have discovered that certain organic compounds will effectively increase the relative volatility between methylene chloride and ethyl ether and permit the separation of methylene chloride from ethyl ether by rectification when employed as the agent in extractive distillation. Table 2 lists the agents that we have found to effective extractive distillation agents to recover methylene chloride from ethyl ether. The data in Tables 2, 3 and 4 was obtained in a vapor-liquid equilibrium still. In every case, the starting material was the methylene chloride-ethyl ether azeotrope which possesses a relative volatility of 1.0. Table 2 lists the relative volatility for each of the agents. The compounds which are effective extractive distillation agents to remove methylene chloride from ethyl ether are methyl acetate, ethyl acetate, n-propyl acetate, isopropyl acetate, isobutyl acetate, n-butyl acetate, n-amyl acetate, isoamyl acetate, ethylene glycol methyl ether, 3-methyl-2-butanone, 3-pentanone, methyl isobutyl ketone, 3-hexanone, 1,4-dioxane, t-butyl alcohol, 4-methyl-2-pentanone, mesityl oxide, 3,3-dimethyl-2-butanone, ethyl butyl ketone, methyl isoamyl ketone, 2-hexanone, propoxypropanol, propylene glycol methyl ether, ethylene glycol methyl ether acetate, nitroethane, nitromethane, 1-nitropropane and 2-nitropropane.

Table 3 lists a number of compounds that proved to be ineffective as extractive distillation agents in the separation of methylene chloride from ethyl ether.

Two of the agents whose relative volatility had been determined in the vapor-liquid equilibrium still were then evaluated in a glass perforated plate rectification column possessing 7.3 theoretical plates and the results listed in Table 4. n-Propyl acetate gave a relative volatility of 2.18 after two hours of operation and propoxypropanol gave a relative volatility of 1.85 after two hours of continuous operation.

THE USEFULNESS OF THE INVENTION

The usefulness or utility of this invention can be demonstrated by referring to the data presented in Tables 1 to 4. All the successful agents show that methylene chloride can be separated from ethyl ether by means of extractive distillation in a rectification column and that the ease of separation as measured by relative volatility is considerable.

TABLE 2

Effective Extractive Agents For Separating Methylene Chloride From Ethyl Ether

| Compounds | Relative Volatility |
|---|---|
| Methyl acetate | 2.2 |
| Ethyl acetate | 1.7 |
| n-Propyl acetate | 2.1 |
| Isopropyl acetate | 1.5 |
| Isobutyl acetate | 1.5 |
| n-Butyl acetate | 1.5 |
| n-Amyl acetate | 1.3 |
| Isoamyl acetate | 1.8 |
| Ethylene glycol methyl ether | 1.5 |
| 3-Methyl-2-butanone | 1.6 |
| 3-Pentanone | 1.6 |
| Methyl isobutyl ketone | 1.5 |
| 3-Hexanone | 1.4 |
| 1,4-Dioxane | 2.1 |
| t-Butyl alcohol | 2.2 |
| 4-Methyl-2-pentanone | 1.7 |
| Mesityl oxide | 1.5 |
| 3,3-Dimethyl-2-butanone | 1.5 |
| Ethyl butyl ketone | 1.4 |
| Methyl isoamyl ketone | 1.5 |
| 2-Hexanone | 1.5 |
| Propoxypropanol | 1.8 |
| Propylene glycol methyl ether | 1.3 |
| Ethylene glycol methyl ether acetate | 1.3 |
| Nitroethane | 1.7 |
| Nitromethane | 1.7 |
| 1-Nitropropane | 1.4 |
| 2-Nitropropane | 1.6 |

TABLE 3

Ineffective Agents For Separating Methylene Chloride From Ethyl Ether

| | |
|---|---|
| n-Propanol | n-Butanol |
| 2-Butanol | t-Amyl alcohol |
| Ethylene glycol ethyl ether | 3-Methyl-1-butanol |
| 2-Methylpentanol | Propylene glycol dimethyl ether |

TABLE 4

| | | Data From Runs Made In Rectification Column | | | |
|---|---|---|---|---|---|
| Agent | Column | Time hrs. | Weight % Ethyl ether | Weight % CH$_2$Cl$_2$ | Relative Volatility |
| n-Propyl | Overhead | 1 | 96.8 | 3.2 | 2.12 |

TABLE 4-continued

| | | Data From Runs Made In Rectification Column | | | |
|---|---|---|---|---|---|
| Agent | Column | Time hrs. | Weight % Ethyl ether | Weight % CH$_2$Cl$_2$ | Relative Volatility |
| acetate | Bottoms | | 12.7 | 87.3 | |
| n-Propyl | Overhead | 2 | 99.4 | 0.6 | 2.18 |
| acetate | Bottoms | | 40.6 | 59.4 | |
| Propoxy- | Overhead | 1 | 77.9 | 22.1 | 1.49 |
| propanol | Bottoms | | 17.4 | 83.6 | |
| Propoxy- | Overhead | 2 | 93.3 | 6.7 | 1.85 |
| propanol | Bottoms | | 13.4 | 86.6 | |

WORKING EXAMPLES

EXAMPLE 1

Sixty grams of the methylene chloride-ethyl ether azeotrope and 30 grams of t-butyl alcohol were charged to a vapor-liquid equilibrium still and refluxed for twelve hours. Analysis indicated a vapor composition of 34.5% ethyl ether, 65.5% methylene chloride; a liquid composition of 19.2% ethyl ether, 80.8% methylene chloride which is a relative volatility of ethyl ether to methylene chloride of 2.2.

EXAMPLE 2

A solution comprising 140 grams of methylene chloride and 60 grams of ethyl ether was placed in the stillpot of a 7.3 theoretical glass perforated plate rectification column. When refluxing began, an extractive agent comprising n-propyl acetate was pumped into the column at a rate of 15 ml/min. The temperature of the extractive agent as it entered the column was 45° C. After establishing the feed rate of the extractive agent, the heat input to the methylene chloride-ethyl ether in the stillpot was adjusted to give a total reflux rate of 40 ml/min. After two hours of operation, overhead and bottoms samples of approximately two ml. were collected and analysed by gas chromatography. The overhead analysis was 99.4% ethyl ether, 0.6% methylene chloride and the bottoms analysis was 40.6% ethyl ether, 59.4% methylene chloride. This gives an average relative volatility of 2.18 for each theoretical plate. This data is presented in Table 4.

EXAMPLE 3

A solution comprising 140 grams of methylene chloride and 60 grams of ethyl ether was placed in the stillpot of the 7.3 theoretical plate column. When refluxing began, an extractive agent comprising propoxypropanol was pumped into the column at a rate of 15 ml/min. The temperature of the extractive agent as it entered the column was 45° C. After establishing the feed rate of the extractive agent, the heat input to the methylene chloride-ethyl ether in the stillpot was adjusted to give a total reflux rate of 40 ml/min. After two hours of operation, overhead and bottoms samples were collected and analysed. The overhead analysis was 93.3% ethyl ether, 6.7% methylene chloride, the bottoms analysis was 13.4% ethyl ether, 86.6% methylene chloride. This gives an average relative volatility of 1.85 for each theoretical plate. This data is presented in Table 4.

We claim:

1. A method for recovering ethyl ether from a mixture of ethyl ether and methylene chloride which comprises distilling a mixture of ethyl ether and methylene chloride in the presence of about one part of an extractive agent per part of ethyl ether-methylene chloride mixture, recovering the ethyl ether as overhead product and obtaining the methylene chloride and the extractive agent from the stillpot, wherein said extractive agent consists of one material selected from the group consisting of methyl acetate, ethyl acetate, n-propyl acetate, isopropyl acetate, isobutyl acetate, n-butyl acetate, n-amyl acetate, isoamyl acetate, ethylene glycol methyl ether, 3-methyl-2-butanone, 3-pentanone, methyl isobutyl ketone, 3-hexanone, 1,4-dioxane, t-butyl alcohol, 4-methyl-2-pentanone, mesityl oxide, 3,3-dimethyl-2-butanone, ethyl butyl ketone, methyl isoamyl ketone, 2-hexanone, propoxypropanol, propylene glycol methyl ether, ethylene glycol methyl ether acetate, nitroethane, nitromethane, 1-nitropropane and 2-nitropropane.

* * * * *